United States Patent  
Park et al.

(10) Patent No.: US 8,246,952 B2  
(45) Date of Patent: *Aug. 21, 2012

(54) METHOD OF INCREASING RADIATION SENSITIVITY BY INHIBITION OF BETA ONE INTEGRIN

(75) Inventors: Catherine Park, San Francisco, CA (US); Mina J. Bissell, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/575,411

(22) Filed: Oct. 7, 2009

(65) Prior Publication Data

US 2010/0034828 A1 Feb. 11, 2010

Related U.S. Application Data

(63) Continuation of application No. 11/628,476, filed as application No. PCT/US2005/019396 on Jun. 2, 2005, now Pat. No. 7,618,627.

(60) Provisional application No. 60/577,252, filed on Jun. 3, 2004.

(51) Int. Cl.
A61K 39/395 (2006.01)

(52) U.S. Cl. .................................................. 424/130.1

(58) Field of Classification Search ........................ None
See application file for complete search history.

(56) References Cited

U.S. PATENT DOCUMENTS

| 5,246,691 | A | 9/1993 | Geerlings et al. |
| 6,123,941 | A | 9/2000 | Bissell et al. |
| 6,165,467 | A | 12/2000 | Hagiwara et al. |
| 6,667,024 | B1 | 12/2003 | Goldenberg et al. |
| 7,618,627 | B2 * | 11/2009 | Park et al. ................ 424/130.1 |
| 2006/0035825 | A1 * | 2/2006 | Wieder ........................... 514/12 |

OTHER PUBLICATIONS

Ole William Petersen, et al., "Interaction with basement membrane serves to rapidly distinguish growth and differentiation pattern of normal and malignant human breast epithelial cells," *Proc. Natl. Acad. Sci USA*, Oct. 1992, vol. 89, 9064-9068.
Yoshikazu Takada, et al., "Identification of a Regulatory Region of Integrin βi Subunit Using Activating and Inhibiting Antibodies", *J. of Biol. Chemistry*, Aug. 1993, vol. 268, No. 23, 17597-17601.
V.M. Weaver, et al., "Reversion of the Malignant Phenotype of Human Breast Cells in Three-Dimensional Culture and In Vivo by Integrin Blocking Antibodies," *J. of Cell Biology*, Apr. 1997, vol. 137, No. 1, 231-245.
Lakshmi Chandrasekaran, et al., "Cell Contact-dependent Activation of α3β1 Integrin Modulates Endothelial Cell Responses to Thrombospondin-1," *Molecular Biology of the Cell*, Sep. 2000, vol. 11, 2885-2900.
Sonali Hemachandra, et al., "Human Monoclonal Antibodies against *Pseudomonas aeruginosa Lipopolysaccharide* Derived from Transgenic Mice Containing Megabase Human Immunoglobulin Loci Are Opsonic and Protective against Fatal *Pseudomonas Sepsis*," *Infection and Immunity*, Apr. 2001, vol. 19, No. 4, 2223-2229.
D.E. Hallahan, et al., "Targeting drug delivery to radiation-induced neoantigens in tumor microvasculature," *J. of Controlled Release*, 2001, vol. 74, 183-191.
Trisha Gura, "Magic bullets hit the target," *Nature*, Jun. 2002, vol. 417, 584-586.
Peter J. Hudson, et al., "Engineered antibodies," *Nature Medicine*, Jan. 2003, vol. 9, No. 1, 129-134.
Judith S. Ochs, "Rationale and Clinical Basis for Combining Gefitinib (Iressa, ZD1839) with Radiation Therapy for Solid Tumors," *Int. J. Radiation Oncology Biol. Phys.*, 2004, vol. 58, No. 3, 941-949.
Catherine C. Park, et al., "Ionizing radiation induces heritable disruption of epithelial cell interactions," *PNAS*, Sep. 2003, vol. 100, No. 19, 10728-10733.
Gerhard Christofori, "Changing neighbors, changing behaviour: cell adhesion molecule-mediated signalling during tumour progression," *The EMBO Journal*, 2003, vol. 22, No. 10, 2318-2323.
ERBITUX™, Package Insert, 2004, Bristol Myers Squibb.
Reju Korah, et al., "Integrin α5β1 Promotes Survival of Growth-Arrested Breast Cancer Cells: An in Vitro Paradigm for Breast Cancer Dormancy in Bone Marrow," *Cancer Res.*, Jul. 2004, vol. 64, 4514-4522.

* cited by examiner

*Primary Examiner* — Ilia Ouspenski

(74) *Attorney, Agent, or Firm* — David J. Aston; Peters Verny, LLP

(57) ABSTRACT

A method for increasing or monitoring apoptosis in tumor cells by the co-administration of ionizing radiation and an anti-integrin antibody. Increasing apoptosis reduces tumor growth in vivo and in a cell culture model. The antibody is directed against the beta-1 integrin subunit and is inhibitory of beta-1 integrin signaling. Other molecules having an inhibitory effect on beta-1 integrin, either in signaling or in binding to its cognate extracellular receptors may also be used. The present method is particularly of interest in treatment of tumor cells associated with breast cancer, wherein radiation is currently used alone. The present method further contemplates a monoclonal antibody suitable for human administration that may further comprise a radioisotope attached thereto.

13 Claims, 9 Drawing Sheets

METHOD OF INCREASING RADIATION SENSITIVITY BY INHIBITION OF BETA ONE INTEGRIN

CROSS REFERENCE TO RELATED APPLICATIONS

This application is a continuation application of U.S. patent application Ser. No. 11/628,476, filed on May 14, 2007 now U.S. Pat. No. 7,618,827, and which is a national stage application of International Patent Application No. PCT/US2005/019396, filed on Jun. 2, 2005, and which claims priority from U.S. Provisional Patent Application No. 60/577,252, filed on Jun. 3, 2004, all of which are hereby incorporated by reference in their entirety.

STATEMENT REGARDING FEDERAL FUNDING

This invention was made with U.S. Government support under Contract Number DE-AC03-76SF00098 between the U.S. Department of Energy and The Regents of the University of California for the management and operation of the Lawrence Berkeley National Laboratory. The U.S. Government has certain rights in this invention.

REFERENCE TO A COMPUTER PROGRAM

Not Applicable.

BACKGROUND OF THE INVENTION

1. Field of the Invention

The present invention relates to the field of radiation and immunomodulation of tumor cells.

2. Description of the Relevant Art

Upon diagnosis of early stage breast cancer, patients are faced with the choice between having 1) a mastectomy (total removal of the breast) or 2) breast-preserving surgery (lumpectomy) and radiation therapy (RT), each resulting in comparable local recurrence rates and overall survival [Reference 1, 2]. RT decreases the risk of local recurrence by ~70%, and remains the standard treatment after lumpectomy [Reference 1]. The typical course of RT after lumpectomy consists of daily treatments of 2.0 Gy per fraction to a total dose of 50-60 Gy. This regimen has largely been derived empirically over time, and has been shown to result in excellent outcomes, with minimal morbidity [Reference 3]. However, the entire course usually requires 6-7 weeks of daily treatments, which often imposes a burden of time and cost that are significant obstacles for many women who are then left with little better alternative than mastectomy. In fact, a survey by the American College of Surgeons reported that in 1999, the majority of women in the United States who were candidates for breast-preservation (lumpectomy plus RT) were undergoing mastectomy! [Reference 4] Indeed, the distance and accessibility to RT centers has been shown to be a significant barrier to treatment [Reference 5]. Thus, in recent years, different strategies have been used to decrease the total time required for RT; these include accelerating treatment (increasing the daily fraction or dose), decreasing treatment volumes and using different RT sources (e.g.) brachytherapy, or the in situ placement of radioactive sources) [Reference 6-9]. These are still investigational, and it may take several years before the optimal approach is determined, in part because late effects of RT may not occur for several years. In addition, the use of accelerated treatment, or larger doses per day, has been shown to increase the risk for late effects [Reference 10, 11]. Thus, while the outcomes of clinical trials are ongoing to test these approaches against one another (a large cooperative trial is planned to begin in the U.S. in 2004, but will not reach maturity for 11 years after accrual, ~2016-2017), it is imperative to investigate novel biologic approaches to improving RT for breast cancer that will increase the efficacy of tumor eradication, while decreasing normal tissue toxicity. This strategy will conceivably lead to decreasing RT doses, making RT less cumbersome and more accessible for patients.

Breast cancer treatment has historically consisted of targeting cancer cells using cytotoxic agents such as chemotherapy and radiation. With the growing recognition that tumors are comprised not only of cancerous cells, but a tumor-promoting microenvironment consisting of many cell types, extracellular matrix (ECM) and stromal factors, novel biologic therapies directed specifically at these targets are being considered and developed. In addition, the ability of tumor cells to adhere to the ECM modify responsiveness to ionizing radiation (IR) [Reference 12] and cell-cell and cell-ECM interactions have been shown to modulate radio sensitivity [Reference 13, 14]. We have previously shown that radiation profoundly influences the ability of mammary epithelial cells to form normal interactions with other cells and ECM [Reference 15]. In particular, single doses of IR resulted in a persistent increase and aberrant expression of β1 integrin, a receptor that is critical in mediating cell-ECM interactions; this observation has been corroborated by others in several tumor cell types [Reference 16, 17]. Furthermore, the increased expression of β1 integrin in response to IR has been shown to be associated with increased radioresistance. β1 integrin belongs to a family of transmembrane receptors that directly mediate cell-ECM interactions (reviewed in [Reference 18, 19]) and are critical in maintaining normal tissue architecture and function.

The family of integrin receptors comprises 18α and 8β subunits that may heterodimerize with each other in various combinations to confer ligand and substrate specificity; the class of β1 integrin receptors is pivotal in signaling cell communication with the microenvironment that governs a wide variety of cellular events including cell growth, apoptosis, adhesion, migration, and differentiation. As is true for many signaling receptors, β1 integrin function depends on the context in which signaling takes place and is different in normal cell and malignant cell context.

In breast cancer, β1 integrin has been implicated in malignant progression in human tissue-based studies as well as in vitro and in vivo models of breast cancer. Studies in human breast cancers, largely based on retrospective analyses of paraffin embedded tissue, indicate that specific heterodimers of β1 integrin are aberrantly expressed as carcinomas become increasingly undifferentiated (Reviewed by Shaw [Reference 20]). The role of β1 integrin as a prognostic factor remains unclear, however, existing data are consistent in describing an association been altered β1 integrin expression and malignant progression. Among in vitro models of breast cancer, β1 integrin has been associated with maintenance of normal tissue architecture [Reference 21, 22], and xenograft models have implicated its role in metastasis [Reference 23, 24].

The primary functional roles of β1 integrin in breast cancer progression have linked β1 integrin expression and signaling associated with growth and differentiation [Reference 21, 25]. These studies indicate that the relative levels of β1 integrin in relationship to other cooperative signaling pathways are important in mediating normal cell-ECM interactions, and the ability of cells to differentiate in 3-dimensional tissue culture. In addition, an emerging body of evidence indicates that β1 integrin plays a significant role in mediating resistance to cytotoxic chemotherapies, not only in breast cancer, but several other cancer cell types, by up-regulating cell survival signals. In particular, β1 integrin mediated adhesion to the ECM has been associated with resistance to cell death [Reference 12, 16, 17, 26], and a cytoprotective effect has been observed against DNA-damaging agents in hematologic malignancies, and lung and breast cancers. Recent studies in vivo using a β1 integrin inhibiting peptide enhanced the effect of 5-FU chemotherapy against colon cancer xenografts [Reference 27].

Antibodies to integrins, and, in particular, β1 integrin, useful in the practice of the present methods, are known in the art. See Bissell et al. U.S. Pat. No. 6,123,941 for a description of reverting malignant phenotype in cancer cells through application of anti-β1 integrin antibody AIIB2. Anti beta-1 integrins against the CD-29 epitope are available from Research Diagnostics, Inc., Flanders, N.J. Another anti-β1 integrin antibody is CSAT, available from the University of Iowa Hybridoma Bank. Another commercially available anti-β1 integrin antibody is 4B7R, a Murine IgG1kappa antibody available from Ancell Immunology Research Products.

Other antibodies (not anti-beta-1) are known for the treatment of cancer, e.g. Herceptin™ antibody (rastuzumab). This antibody attaches to breast cancer cells which possess a receptor site called HER2/neu. RT has been suggested for use with Herceptin, but little data exist as to the desirability of such combination treatments.

RT is generally offered to breast cancer patients to rid the body of any microscopic cancer cells that may remain near the area where the cancer was originally receptor. Chemotherapy of cancer is often combined with radiation therapy. Although there have been efforts to combine biologic agents with radiotherapy, including monoclonal antibodies against the epidermal growth factor receptor (EGFR) in head and neck cancers, and lung carcinomas, little is known about the safety or efficacy of such treatments.

The usual course of RT includes daily treatments five days a week for five to seven weeks. Each session generally lasts an hour or less. Radiation therapy works by causing changes at the molecular level in tissues where the radiation beam is targeted. Giving all the radiation needed at one time would cause significant and irreparable damage not only to cancer cells, but also to normal cells. However, giving small doses of radiation each day enables the majority of healthy cells to repair any damage, while rendering cancer cells inactive.

In combining the present anti-integrin and radiation treatments, other known radiation therapies may be employed. One possibility is to administer the radiation as intraoperative radiation therapy. Another possibility is to administer the radiation through radioisotopes coupled to the anti-integrin agent. As another possibility, high-dose rate brachytherapy, which is a new form of internal radiation therapy, may be employed. This aggressive, comprehensive approach to cancer treatment frequently uses internal radiation therapy for cancers of the lung, breast, prostate, rectum, cervix, and uterus. Brachytherapy is a quicker, more effective way to give radiation therapy treatments. Brachytherapy as a radiation therapy places the radiation in the tumor, tightly concentrated within the site of the cancer. This radiation therapy technique allows that the maximum radiation dose is received where it is needed most, while allowing little radiation to effect the surrounding healthy tissue. In many cases, brachytherapy is an effective radiation therapy alternative to surgical removal of a tumor and the affected organ, and may be used in connection with the present methods.

BRIEF SUMMARY OF THE INVENTION

The present invention is directed to a method of modifying cellular responses to ionizing radiation, involving radiation wherein a cell is adherent to an extracellular matrix which contains ligands binding to cellular β1 integrin. A cellular response of particular importance is apoptosis, which is a programmed cell death that is a goal of radiation therapy of human cancer. Another cellular response is proliferation, which may be measured, e.g., by tumor size. The present methods have a variety of uses in scientific research as well as applicability to human health care.

The present methods comprise the step of delivering to a cell, cell line, or tissue an inhibitory anti-β1 integrin composition. The preferred composition is an inhibitory antibody that blocks the function of the β1 integrin, particularly insofar as it involves adhesion to the extracellular matrix and/or intracellular signalling. The preferred anti-β1 integrin composition is a human or humanized monoclonal antibody, but it may also comprise an antibody fragment or inhibitory peptide.

The present methods further comprise the step of delivering to the cell ionizing radiation. This ionizing radiation is generally of the type used in cancer therapy and is intended to destroy or inhibit the ability of tumor cells to reproduce. The radiation step may be carried out before, during or after delivering said anti-β1 integrin composition.

It is contemplated that the radiation will be delivered in doses of 2-8, preferably 2-6 Gy per day. Further it may be delivered at a rate of 0.25 to 6 Gy per minute. One method contemplates that delivering radiation is carried out after delivering said anti-β1 integrin composition. The ionizing radiation may be in a total dose of 2-20 Gy in one day, or in fractions in different days in the range of 0.1 to 6 Gy per day and up to 30 days. For higher radiation doses, it is preferred that administration of the anti-integrin composition precede the radiation.

The present method is applicable to cells comprising any type of tumor having β1 integrin receptors, but it is particularly applicable to tumors in cells adherent to an extracellular matrix, and most particularly to tumors involving human breast epithelial cells.

The present method is useful in evaluating the proliferation and apoptotic properties of a test cell that may be malignant. Its response to ionizing radiation and anti-β1 integrin antibody will vary depending on the malignancy of the cell. As discussed below, malignant cells are more susceptible to IR in combination with the antibody. The present method is also applicable to treating human patients with carcinomas, especially breast cancer. The patient receives a dose of an anti-β1 integrin antibody in conjunction with a course of IR therapy. The IR is given in a dose effective to reduce cellular growth; and the anti-integrin composition causes an additional reduction in tumor growth. Tumor growth may be measured by physical size; cellular proliferation may also be measured by assays such as the Ki-67 assay.

The term antibody is used in a broad sense, defined below. Inhibitory peptides may also be used in place of an antibody as a composition which binds to and antagonizes the signaling and/or adhesion mediated by β1 integrin.

DETAILED DESCRIPTION OF THE PREFERRED EMBODIMENT

1. Introduction

Figure 1:
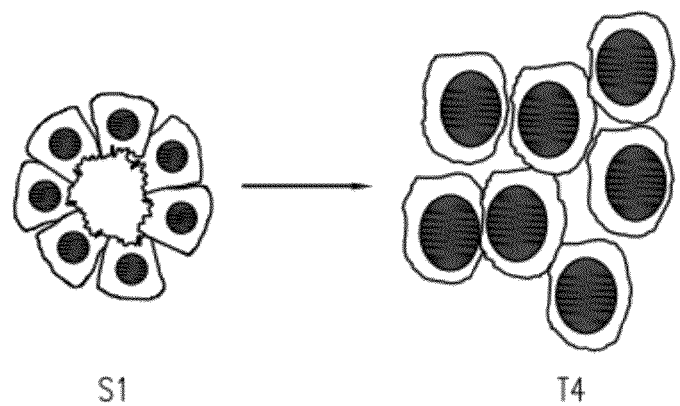
FIG. 1 is a sketch showing the visual model of HMT 3522 breast cancer progression from S1 (nonmalignant cell line) to T4 (malignant cell line)

As discussed above, the present inventors have found that inhibiting β1 integrin signaling may improve the efficacy of cytotoxic agents such as radiation by abrogating β1 integrin mediated resistance to apoptosis. In addition, via effects on cell-ECM interactions and stroma, inhibiting β1 integrin may modulate the response of tissues to ionizing radiation. The inventors suggest that β1 integrin inhibition, using monoclonal antibody, AIIB2, will increase the efficacy of radiation in breast carcinoma and other cancers and will increase the therapeutic efficacy of radiation therapy.

The table below shows the involvement of β1 integrins in a variety of cancer types. It is contemplated that the present methods of modifying cellular response are applicable to all types of cancer wherein beta integrins play a role in drug resistance.

TABLE 1

| β1 integrin mediated drug resistance | | | |
|---|---|---|---|
| Cancer | Agents Tested | Mechanism | Integrins involved |
| Breast cancer [Reference 28] | Paclitaxel | AKT activation | α5β1, α2β1 |
| CML [Reference 29, 30] | VCR, STI-571, α interferon | AKT activation | α5β1 |
| MultipleMyeloma [Reference 31, 32] | Doxorubicin, Melphalan | P27 expression | α4β1 |
| Small cell lung cancer [Reference 26] | Doxorubicin, cisplatin | unknown | α2β1, α3β1, α6β1 |

It has been shown that individuals with BRCA 1/2 mutations are also at higher risk for ovarian, pancreatic, prostate and stomach cancers in addition to breast cancer, suggesting a genetic relationship between certain forms of these cancers. Colon cancer has also been shown to have enhanced metastatic activity associated with increased β1 integrin expression. See, Okazaki et al, Enhancement of metastatic activity of colon cancer as influenced by expression of cell surface antigens, J. Surg. Res. 78(1): 78-84 (Jul. 15, 1998). Lymphomas involving cells expressing β1 integrin may also be treated.

2. Materials Methods and Definitions

Ionizing Radiation

The term "ionizing radiation" (IR) as used in connection with the present invention may refer to X-rays, gamma rays, or the use of fast moving subatomic particles directed at target tissues for purposes of reducing the viability of such tissues. They may be delivered from an external source or from an internal implant at the site of the target tissue. When using X-ray, clinically relevant doses are preferred, and these may be applied in single doses or fractionated, as is known in the art. Ionizing radiation may be delivered by coupling of radioactive isotopes to delivery molecules, including the present anti-β1 integrin antibody or antibody fragment. The radiation may be directed to the tumor by any guidance procedure, typically involving computed tomography (or CT) images taken shortly before treatment. The patient's body is marked on the skin to indicate where the radiation should be directed. In some centers, the patient also is positioned to lie in a body mold as an extra measure to try to make sure the tumor is in the location indicated by the earlier CT scans. A margin around the tumor is included in the radiation target area to avoid missing any part of a tumor.

Anti-Integrin Antibody

AIIB2 is a rat monoclonal IgG$_1$ that was originally isolated from a human choriocarcinoma hybridoma, and identified as an anti-β1 integrin antibody that non-specifically bound to all heterodimers of the β1 integrin extracellular domain [References 36-38]. Experiments using F(ab)' fragments of enzyme-digested AIIB2 indicated that the epitope-binding portion of the antibody was active, and resulted in down modulation of β1 integrin mediated signaling and downstream signaling intermediates [Reference 22, 39]. β1 integrin biology is made more complex by 5 known splice variants that differ primarily with regard to the cytoplasmic domain [reviewed in Reference 40], further described below in connection with polypeptides for immunization in preparing an anti-β1 integrin antibody. AIIB2 has been found to recognize all variants via the extracellular domain.

An anti-integrin antibody suitable for use with the present method may be produced by methods similar to those described in Werb, Z., Tremble, P., Berensten, O., Crowley, E., and Damsky, C. H. (1989). Signal transduction through the fibronectin receptors induces collagenase expression. J. Cell Biol. 109, 877-890; and Damsky, C. H., Fitzgerald, M., and Fisher, S. J. (1992). This provides a screening assay for potential antibodies. The immunogen used was whole human JAR choriocarcinoma cells. The antibody blocks cell attachment to Fn, Col-I, IV and LN, and so can be further characterized in these ways.

The term "human monoclonal antibody" as used herein, refers to an antibody substantially free of non-human (e.g. mouse) sequence. It may be fully human, or humanized, as is known in the art, by the removal of mouse sequences save for the binding regions of the antibody, either the Fv portion or the CDR regions.

The term "antibody," as used herein, further includes various forms of modified or altered antibodies, such as various fragments such as an Fv fragment, an Fv fragment containing only the light and heavy chain variable regions, an Fv fragment linked by a disulfide bond (Brinkmann, et al. Proc. Natl. Acad. Sci. USA, 90: 547-551 (1993)), a Fab or (Fab)'2 fragment containing the variable regions and parts of the constant regions, a single-chain antibody and the like (Bird et al., Science 242: 424-426 (1988); Huston et al., Proc. Nat. Acad. Sci. USA 85: 5879-5883 (1988)). The antibody may be originally of animal (especially mouse or rat) or human origin or may be chimeric (Morrison et al., Proc Nat. Acad. Sci. USA 81: 6851-6855 (1984)). It may be humanized as described in Jones et al., Nature 321: 522-525 (1986), and published UK patent application #8707252.

Single chain recombinant antibodies may also be used, as described, for example in U.S. Pat. No. 5,840,300 to Williams et al, entitled "Methods and compositions comprising single chain recombinant antibodies," hereby incorporated by reference for purposes of describing methods useful in the preparation of such compositions. Briefly, Kappa, heavy, and lambda immunoglobulin chains are amplified separately and are subsequently combined as single chains, using recombinant PCR, i.e., the splicing by overlap extension (SOE) PCR method, wherein the single chains comprise a heavy chain plus a kappa chain or a heavy chain plus a lambda chain. Flexible linear-linker peptides are used in the primers which therefore comprise the linker used to join VL to VH to form the novel recombinant Fv fragments containing integrin binding variable regions comprising both light and heavy chains as a single chain. The Fv fragments may be developed as a library of Fv fragments directed against β1 integrin subunits.

Suitable antibodies can also be prepared in genetically engineered mice designed to express human antibodies. The mice can be immunized with an antigen comprising a fragment of human β-1 integrin and the mouse splenocytes containing active B cells fused with a suitable myeloma line. Mice with the human Ig repertoire are commercially available. See Hemachandra et al., Human Monoclonal Antibodies against *Pseudomonas aeruginosa* Lipopolysaccharide Derived from Transgenic Mice Containing Megabase Human Immunoglobulin Loci Are Opsonic and Protective against Fatal Pseudomonas Sepsis, INFECTION AND IMMUNITY, April 2001, p. 2223-2229 Vol. 69, No. 4.

Another technique for preparing the present antibodies, phage display combinatorial library technology, provides a useful method to generate large libraries of human Mabs that may be screened for anti-integrin activity. The libraries made from lymphocyte mRNA may consist of up to $10^8$ recombinants of monoclonal Fab repertoires. By displaying the library on a filamentous phage surface and panning against a model epitope (β1 integrin fragment as described below), monoclonal Fab antibodies can be selected and analyzed for their immunological properties and biological activities (integrin inhibition). Fabs are ideal for use in both therapeutic and diagnostic methods as they can be produced in large quantities inexpensively and they are innately non-immunogenic. See U.S. Pat. No. 6,716,410 to Witzum et al. for a description of this technique, which is hereby incorporated by reference.

As described by Marks et al., a human single-chain Fv (scFv) may be isolated from a non-immune phage library which binds the β1 antigen. CDR3 of the light (V(L)) and heavy (V(H)) chain variable region of a selected antibody may then be sequentially mutated, the mutant scFv displayed on phage, and higher affinity mutants selected on antigen. See Schier et al., "Isolation of picomolar affinity anti-c-erbB-2 single-chain Fv by molecular evolution of the complementarity determining regions in the center of the antibody binding site," J Mol Biol. 1996 Nov. 8; 263(4):551-67.

Bispecific antibodies (e.g. diabodies) which cross link with other antigens may also be employed. Unlike other bispecific formats, diabodies can be produced in functional form by secretion from bacteria (*E. coli*) or yeast (*P. Pastoris*). Detailed protocols can be found in: Tomlinson I. and Holliger P. (2000) Methods for generating multivalent and bispecific antibody fragments, *Methods Enzymol,* 326, 461-479; and Holliger, P. (2001) Expression of antibody fragments in *Pichia pastoris. Meth. Mol. Biol.* Dimeric antibody fragments, or minibodies, may be created in a variety of known ways. These produce noncovalent or covalent dimers (sc(FV)2). The present antibody composition may be prepared as a purified pharmaceutical composition with known stabilizers and excipients in a sterile powder or liquid form for intravenous administration as is known in the art and exemplified in the description of a freeze dried monoclonal antibody in U.S. Pat. No. 6,165,467, hereby incorporated by reference.

Apoptosis

The term "apoptosis" is used herein in its conventional sense. Apoptosis is defined as a normal physiologic process of programmed cell death which occurs during embryonic development and during maintenance of tissue homeostasis. The process of apoptosis can be subdivided into a series of metabolic changes in apoptotic cells. Individual enzymatic steps of several regulatory or signal transduction pathways can be assayed to demonstrate that apoptosis is occurring in a cell or cell population, or that the process of cell death is disrupted in cancer cells. The apoptotic program is also observed by morphological features which include changes in the plasma membrane (such as loss of asymmetry), a condensation of the cytoplasm and nucleus, and internucleosomal cleavage of DNA. This is culminated in cell death as the cell degenerates into "apoptotic bodies".

Apoptosis is measured by a standard assay known as the TUNEL assay. One of the hallmarks of late stage apoptosis is the fragmentation of nuclear chromatin. The DNA degradation generates DNA strands with exposed 3'-hydroxyl ends. The TUNEL assay detects apoptosis-induced DNA fragmentation through a quantitative fluorescence assay. Terminal deoxynucleotidyl transferase (TdT) catalyzes the incorporation of bromo-deoxyuridine (BrdU) residues into the fragmenting nuclear DNA at the 3'-hydroxyl ends by nicked end labeling. A TRITC-conjugated anti-BrdU antibody can then label the 3'-hydroxyl ends for detection by a fluorescence detection instrument.

Another apoptotic assay is Annexin-V detection. Normally, phosphotidylserine (PS) is localized on the inner membrane of the plasma membrane. However, during the early stages of apoptosis, externalization of PS takes place. Annexin-V is a calcium binding protein which binds to PS and can be observed with annexin-V-FITC staining by flow cytometry. The ability of cells treated with compounds described in the literature to bind annexin-V, is taken as an indication that cells were undergoing apoptosis.

3-D Cell Culture Model

A model of human breast cancer progression, HMT-3522, originally derived from a woman with benign fibrocystic breast disease, from which both non-malignant S1 cell lines and tumorigenic T4 cell lines were derived was used in the present work [Reference 33]. When cultured in a 3-dimensional (3-D) basement membrane rich matrix (Matrigel™ artificial cell matrix), the non-malignant cell line, S1, undergoes morphogenesis and after 7 days, forms acinar-like structures with polarized cells, a central lumen and basement membrane, recapitulating normal ductal structures found in vivo. In contrast, T4 and MDA-MB-231 cells, both malignant cell lines, continue to proliferate and form disorganized tumor colonies when plated in Matrigel. Thus, this model is capable of distinguishing between non-invasive mammary epithelial cells (S1) and invasive tumorigenic cells by their growth characteristics when plated in 3-D using Matrigel.™

Matrigel is a synthetic form of extracellular matrix. The "extracellular matrix" ("ECM") is an in vivo collection of molecules that, in vertebrates, is the complex mixture of proteins, proteoglycans, and, in the case of bone, mineral deposits, that contact cells. Almost all of the proteins of the ECM are glycoproteins, such as collagens, laminins, and fibronectin. The ECM also contains elastins, which are not glycosylated. Proteoglycans are also glycoproteins but consist of much more carbohydrate than protein; that is, they are huge clusters of carbohydrate chains often attached to a protein backbone. Cells attach to the ECM by means of transmembrane glycoproteins called integrins. The extracellular portion of integrins binds to various types of ECM proteins: collagens, laminins and fibronectin. The intracellular portion of the integrin molecule binds to the actin filaments of the cytoskeleton.

FIG. 1 illustrates the prior art HMT 3522 cell culture model. The non-malignant human breast cancer epithelial cell line HMT 3522 may proceed from a normal S1 subtype to a visibly malignant subtype (termed T4). S1, non-malignant mammary epithelial cells undergo morphogenesis and form acinar like structures in 3-D. In contrast, T4, malignant cells, form tumor-like disorganized and invasive colonies. This assay, which models the three dimensional environment of cultured cells, is generally regarded as predictive of in vivo behavior of malignant cells.

β1 Integrin

Integrins belong to a large family of cell surface proteins commonly referred to as glycoproteins. Integrins are composed of noncovalently associated α and β subunits which make up heterodimers: the larger termed α chain and the smaller β chain. At least 16α subunits and 8β subunits are expressed, which can give rise to 22 different integrins. Integrins are thought to play critical roles in cell migration, differentiation, and survival. There is now considerable evidence that these transmembrane receptors play an important role in the regulation of gene expression and signal transduction. Excellent reviews of integrin structure, function, and ligand specificity may be found in: Hynes, R. 1992. Cell 69:11-25; Kramer, R. 1993. "Integrin Structure and Ligand Specificity in Cell-Matrix." Interactions" in Molecular and Cellular Aspects of Basement Membranes.

The β1 integrin is found in any transmembrane protein that has this component as part of the heterodimer.

3. The Present Method

The present method comprises the administration of an anti-β1 integrin antibody in conjunction with a cytotoxic dose of IR. The antibody may be administered intravenously or by other known means, or delivered directly to a tumor to be treated.

The optimal schedule and dosing of IR in conjunction with the antibody may be determined by routine experimentation using the tests described herein. In addition, the antibody may be coupled to sources of IR to provide the combination effect. It is preferred; however, that the IR be delivered to the tumor after the antibody has had time to disrupt ECM binding. The apoptotic effect of the radiation is thereby significantly increased over the effect of the radiation without the antibody. Furthermore, as described below, the apoptotic effect is more significant in tumor cells than in normal cells.

The antibody may be one of a wide variety of agents, as encompassed by the definition given herein, but it is important that the antibody be antagonistic to the function of the β1 integrin. That is, the antibody should inhibit the signaling between the integrin and the extracellular matrix.

EXAMPLES

Example 1

FIG. 2

β1 Integrin Expression is Persistently Increased in Progeny of Human Mammary Epithelial Cells After Single Doses of Ionizing Radiation.

Figure 2A:
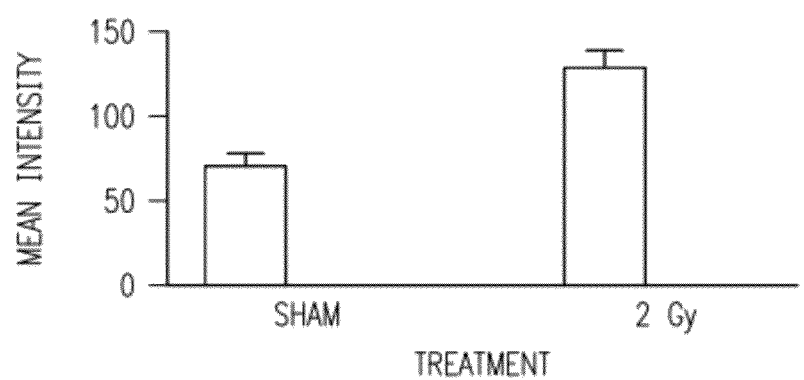
FIG. 2 is an immunoblot showing upregulation of β1 integrin in irradiated cells (bottom panel); a and bar graph showing intensity of anti-β1 integrin staining (top panel)
Figure 2B:
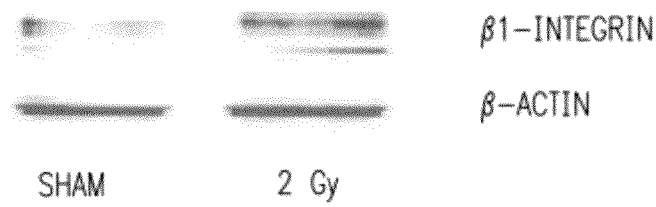

Referring now to FIG. 2, it can be seen that the progeny of human mammary epithelial cells (S1) exposed to single doses of ionizing radiation (2 Gy) in 3-D culture upregulate expression of β1 integrin, shown in FIG. 2 (bottom) by immunohistochemistry and in protein immunoblot analysis [Reference 15]. FIG. 2B shows blots wherein the treated cells show an approximately two fold increase in mean intensity. The bar graph at the top panel of FIG. 2 shows nearly a two fold intensity of staining for beta-1 integrin after 2 Gy radiation treatment of the S1 cells.

This phenotype was shown to persist for multiple generations of daughter cells among surviving colonies. These findings are consistent with other reports of IR-induced integrin expression [Reference 16, 34, 35], and implicate cell-ECM interactions as a mechanism of IR response in human mammary epithelial cells. This data, together with the fact that β1 integrin was shown to modulated response to cytotoxic therapies, provided the background for us to investigate β1 integrin as a target to enhance the therapeutic effect of RT.

Example 2

FIG. 3

β1 Integrin Inhibition Results in Enhanced Dose-Dependent IR Induced Apoptosis in 2-D Culture Initial studies began by testing the effect of AIIB2, a β1 integrin inhibitory antibody, with escalating doses of IR in human mammary epithelial cells plated on standard tissue culture plastic. Mammary epithelial cell lines, S1 (non-malignant) and T4 and MDA-MB-231 (malignant) were used. Cells were plated on Day 0, and 0.08 mg/ml AIIB2 was added at Day 2, media was washed prior to IR exposure delivered at ~2 Gy/minute using a Cesium source on Day 3. Cells were assayed for apoptosis on Day 4 using fluorescence-activated cell sorting (FACS) analysis for TUNEL and Annexin V immunoreactivity. For all cell lines, AIIB2 alone resulted in increased apoptosis, and the combination of AIIB2 and IR resulted in an IR dose-dependent increase in apoptosis (FIG. 3).

Figure 3C:
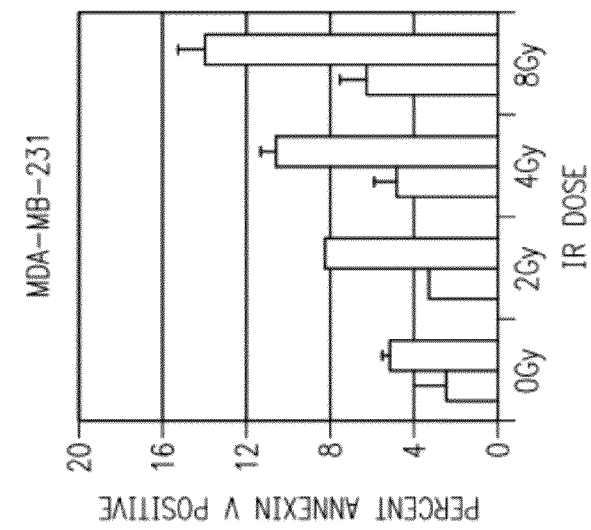
FIG. 3 is a series of three bar graphs showing degrees of apoptosis of, from left to right, S1 (nonmalignant) (3A), T4 (malignant) (3B) and MDA-MB-231 (invasive and hormone independent human breast cancer line) (3C) cells after varying IR doses (solid bars on left) compared with IR plus anti-β1 integrin antibody (AIIB2) pretreatment (hatched bars on right)
Figure 3B:
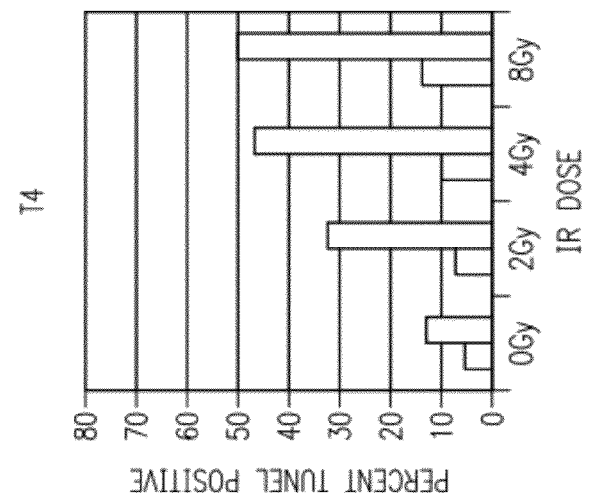
Figure 3A:
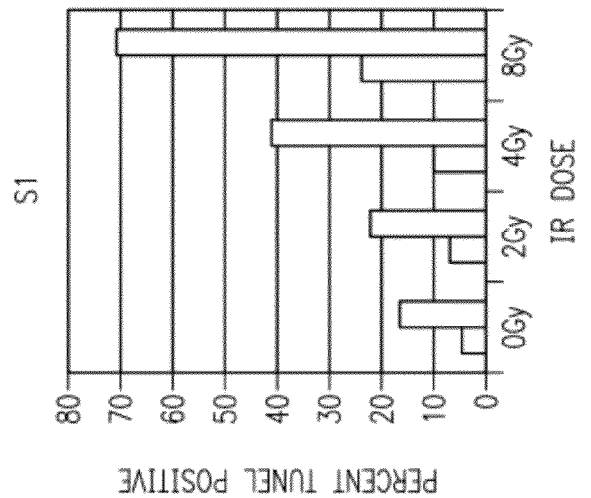

Referring now to FIG. 3, the three bar graphs show apoptosis (TUNEL assay) after different IR doses in malignant S1 cells (3A) and malignant T4 cells (3B). Malignant MDA-MB-231 cells (3C) were measured for increased Annexin V immunoreactivity, which is also indicative of apoptosis.

The S1, T4 and MDA-MB-231 cells were plated on standard tissue culture plastic and treated with 0.08 mg/ml AIIB2. Media was washed and cells irradiated with increasing doses from 0-8 Gy before assaying for TUNEL or Annexin V by FACS analysis.

As shown in the graphs, a combination of IR and the anti-integrin antibody produces a 3-4 times greater apoptosis than IR alone. Furthermore, significantly more apoptosis is observed in the malignant cells than in the non-malignant cells, particularly at the 2-4 Gy range.

Example 3

FIG. 4

Expression of β1 Integrin in a Variety of Cell Lines

Both T4 and MDA-MB-231 cell lines overexpress β1 integrin compared to S1, non-tumorigenic cells. To address whether or not β1 integrin expression predicted the response to AIIB2 treatment, also tested were several other breast cancer cell lines for β1 integrin expression, as shown in FIG. 4. Six cell lines (S1, T4, MDA-MB-231, SKBR3, BT474 and MCF-7) were assayed for total β1 integrin expression using Western immunoblot, and demonstrated different levels of expression. These cell lines were tested for response to AIIB2, at both low and high doses of antibody as indicated below. Controls included on-specific rat IgG (Pierce) indicating that response to AIIB2 was specific. All malignant cell lines, regardless of β1 integrin expression level, responded similarly to AIIB2 with increased apoptosis and decreased proliferation (FIG. 4). Therefore, in this in vitro model, β1 integrin expression level did not predict for response to inhibition using AIIB2.

The following cell lines were tested by Western blot, with the following results (data not shown):

| Cell line | Blot |
| --- | --- |
| S1 | weak |
| T4 | strong |
| MDA231 | strong |
| SKBR3 | very faint |
| MCF-7 | faint |
| BT474 | faint |

Figure 4B:
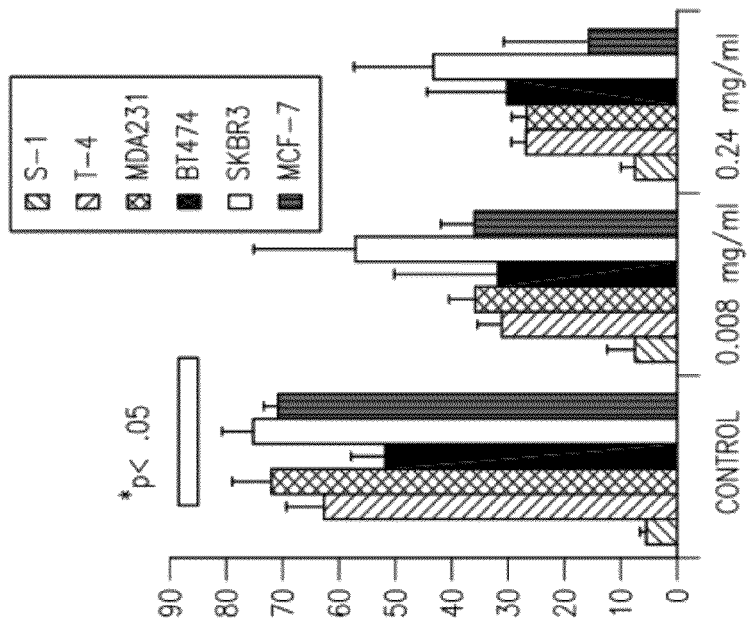
FIG. 4 is a pair of bar graphs showing apoptotic (TUNEL) response (4A) and cytostatic (Ki-67) responses (4B) to six different cell lines anti-β1 integrin antibody, said responses being increased apoptosis and decreased cell proliferation despite varying degrees of integrin expression; 4A is % apoptosis in three dimensional cell culture (3D) and 4B is cytostatic response in 3D.
Figure 4A:
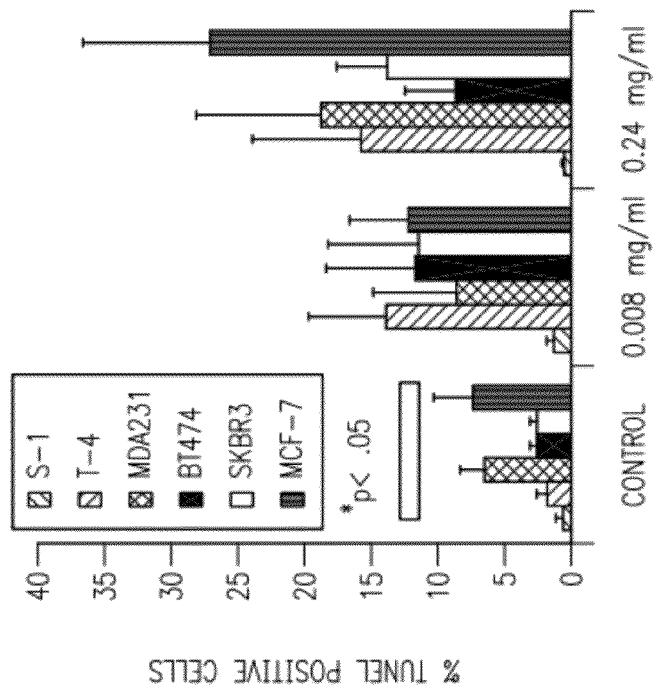

As shown in FIG. 4, the apoptosis induced by the anti-integrin antibody (FIG. 4A) and the cytostatic response (FIG. 4B) for the different cell lines showed that the anti-integrin antibody tended to have greater effect in the more malignant cells. Antibody was added at either 0.08 mg/ml or 0.24 mg/ml to cells grown in the three dimensional Matrigel assay. Increased apoptosis and decreased proliferation was observed among malignant cells in response to AIIB2 regardless of β1 integrin expression. That is, in each case, it can be seen that the apoptosis and Ki-67 response as significantly greater in the presence of the anti-integrin antibody than in the control. Ki-67 is a commercially available monoclonal antibody that reacts with a nuclear antigen expressed in proliferating cells but not in quiescent cells. Expression of this antigen occurs preferentially during late G1, S, G2, and M phases of the cell cycle, while in cells in G0 phase the antigen cannot be detected. Consequently, the antibody is used in tumor pathology to detect proliferating cells in neoplastic diseases.

Example 4

FIG. 5

β1 Integrin Inhibition Enhances Radiation-Induced Apoptosis of Malignant Tumors in 3-D Culture The effect of IR alone and the effect of IR and anti-integrin antibody was examined in three dimensional cell culture of S1 non-malignant and MDA-MB-231 malignant cells lines. S1 acinar structures showed no discernible change with increasing doses of IR alone, while MDA-MB-231 cells responded with increased apoptosis with IR dose. The addition of AIIB2 to IR increases the apoptotic response to IR in this model.

Cells were cultured in 3D, as described above, and 24 hours prior to IR, 0.08 mg/ml of AIIB2 was added to the cultures and media was changed before irradiation. This dose range was chosen as it had an inhibitory effect on cell proliferation, but did not induce substantial apoptosis. Cells were exposed to increasing doses of ionizing radiation using a Cesium source at ~2 Gy/minute. Distinct from the classic colony formation assay, this model investigates the longer term or persistent effect of IR, several days after colonies have been exposed to treatments.

Figure 5A:
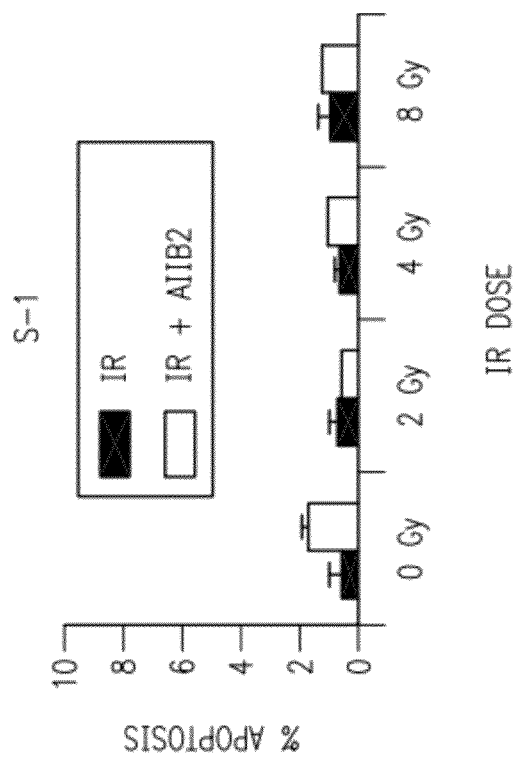
FIG. 5 is a pair of bar graphs showing increase in apoptosis in S-1 non-malignant cells (left panel) vs. MDA-MB-231 malignant cells (right panel) under conditions of IR alone and IR+AIIB2 antibody.
Figure 5B:
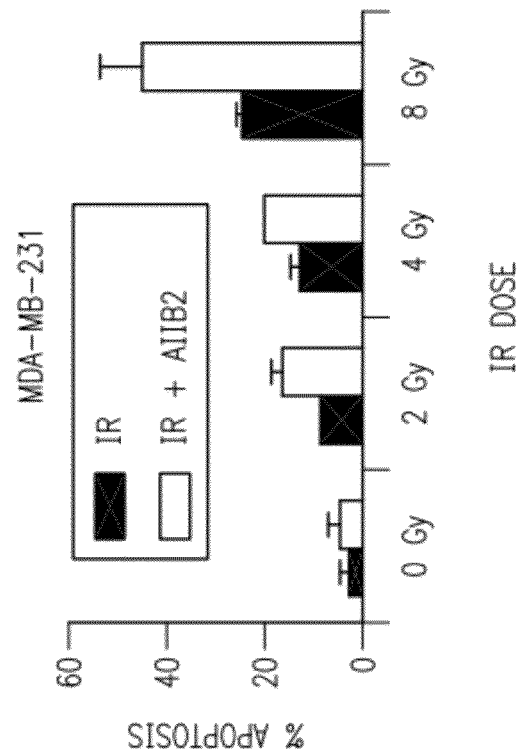

FIG. 5 shows that the combination of IR plus anti-integrin antibody has more effect on the more malignant MDA-MB-231 cells than the non-malignant S1 cells, at a variety of doses of IR.

Example 5

FIG. 6

AIIB2 Results in Decreased Tumor Formation, Increased Apoptosis and Cytostasis In Vivo To determine the optimal dose of anti-integrin antibody AIIB2 that had activity against human breast cancer in vivo, the ability of AIIB2 to 1) inhibit tumor formation and 2) affect formed tumors in vivo using T4 xenografts was tested. Adult female nu –/– mice were implanted with 2×10e7 T4 cells either subcutaneously or into the mammary fat pad on Day 0. Three groups of mice began receiving biweekly intraperitoneal injections (i.p.) of 1) Control IgG, 2) 1 mg/kg AIIB2 or 3) 5 mg/kg AIIB2 in a blinded fashion. Tumors were measured and volume was estimated by multiplying width×length× depth, measured bi-weekly.

After 4 weeks, animals were sacrificed and histologic analysis of tumors was performed, assaying for apoptosis by TUNEL assay, and proliferation by Ki-67. Three additional groups of mice were implanted with tumor cells at Day 0 and tumors were allowed to grow for 4 weeks. Animals were stratified according to tumor size and randomized to receive biweekly i.p. injections of 1) Control was 5 mg/kg of non-specific rat IgG 2) 1 mg/kg AIIB2 or 3) 5 mg/kg AIIB2 in a blinded fashion. Tumor measurements were taken biweekly, and animals were sacrificed and tumors were analyzed as described above. This experiment has been performed 2 times.

Figure 6A:
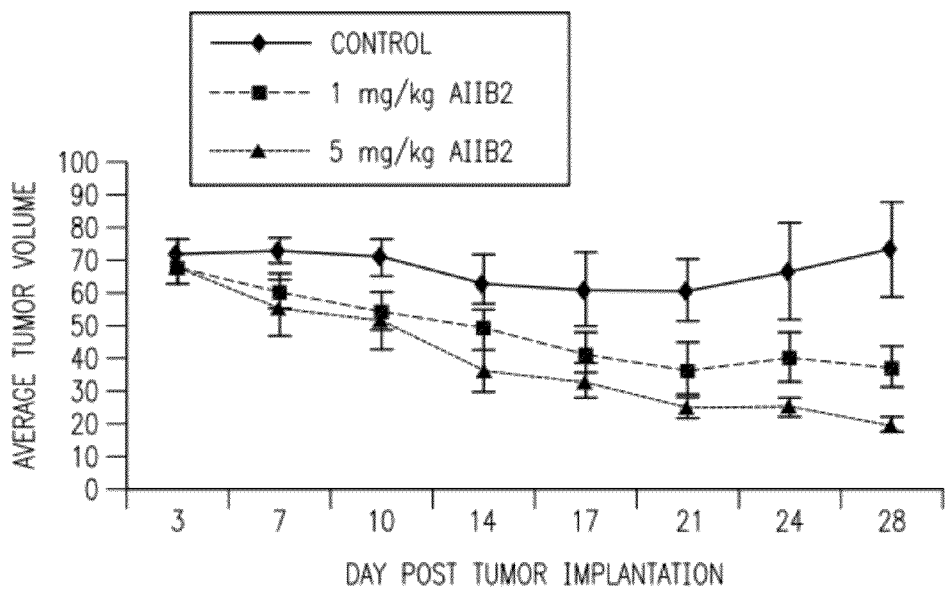
FIG. 6 is a line graph (6A) showing average tumor volume as a function of treatment with anti-β1 integrin antibody, showing the inhibition of T4 xenograft tumor formation in vivo, and a bar graph (6B) showing the histological response to an anti-β1 integrin antibody on cell proliferation (Ki-67 assay) and apoptosis (TUNEL assay); Ki67 bars are on the left.

AIIB2 significantly inhibited formation of T4 tumors at both 1 mg/kg and 5 mg/kg doses compared to animals receiving non-specific control rat IgG according to average tumor volume. FIG. 6A shows a comparison of average tumor volume in a control versus mouse treated with either 1 mg/kg or 0.5 mg/kg AIIB2 antibody. As can be seen in the lines with squares (1 mg/kg) and triangles (5 mg/kg), after 28 days the average tumor volume was only approximately ½ that of untreated animals.

Figure 6B:
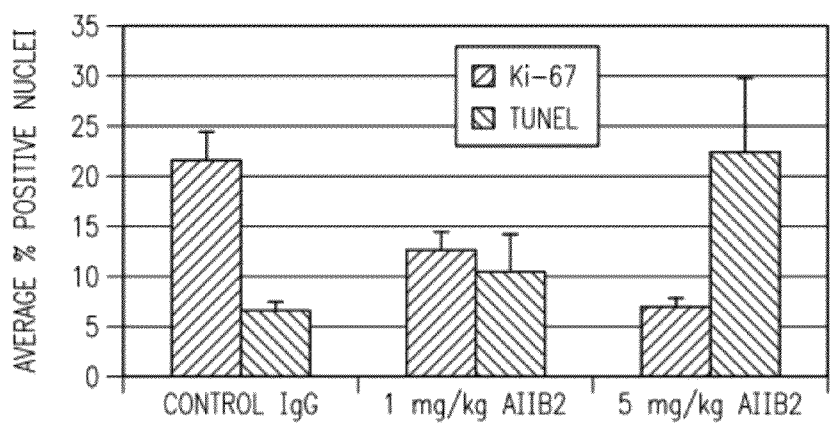

Also, histologic analysis revealed a significantly increased percentage of TUNEL positive cells among the treated groups versus controls, and a significantly decreased percentage of Ki-67 positive cells among treated groups versus controls (FIG. 6B). Increased apoptosis and decreased proliferation in a dose-dependent manner resulted.

In addition, AIIB2 was associated with significantly increased apoptosis and cytostasis among formed tumors, at both 1 mg/kg and 5 mg/kg, again in a dose-dependent manner. However, tumor size did not significantly change between control and treated groups. Histologically, one observes a central and cystic pattern of apoptosis and necrosis of the tumor, which may account for moderate change in the measured size. In both arms of the study, animals tolerated treatment without any signs of toxicity; there were no differences in animal weight per group, size or observed activity. Occasional animals developed dry skin, however, this was not significantly correlated with treatment and there was no mortality attributable to treatment.

The foregoing example indicates that AIIB2 is active in vivo, resulting in apoptosis and cytostasis among treated tumors in vivo as well as in vitro. Results from combining the antibody with radiation may be reasonably be expected to have results in vivo similar to those observed experimentally in cell culture.

Example 6

Figure 7:
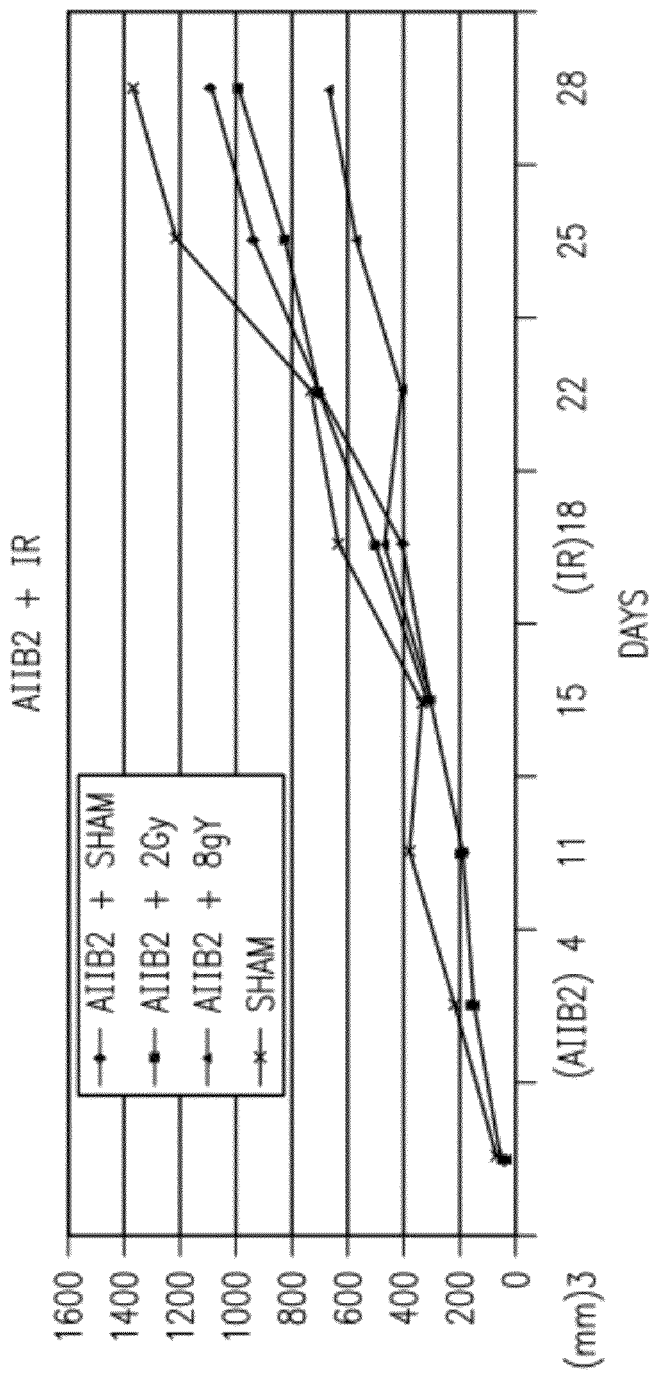
FIG. 7 is a line graph showing tumor volume in an experiment in which anti-integrin antibody is administered to mice with implanted tumors, followed by different doses of IR.
Figure 8:
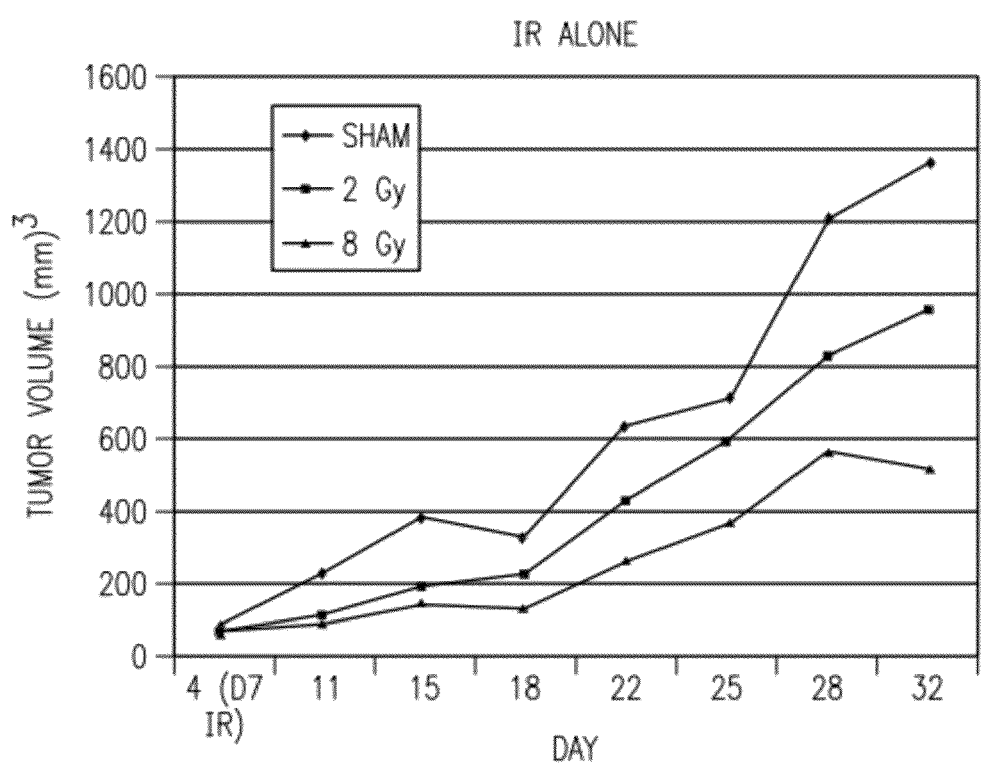
FIG. 8 is a line graph showing tumor volumes as in FIG. 7 when IR alone is administered to mice with implanted tumors.

FIGS. 7 and 8

In Vivo Treatment of Tumors with Anti-Integrin Antibody Followed by IR

Results from experiments conducted with mice receiving anti-integrin antibody followed by different doses of IR are shown in FIG. 7.

Adult female nu −/− mice were implanted with $2 \times 10^7$ MCF-7M1 cells either subcutaneously or into the mammary fat pad on Day 0. Four groups of mice are represented: those receiving AIIB2+sham irradiation (i.e. going through the radiation protocol with no radiation); AIIB2+2 Gy radiation; AIIB2+8 Gy radiation; and a control group receiving IgG and no (sham) radiation. In each case, antibody was administered on day 4. The mice received intraperitoneal injections (i.p.) of either Control IgG or 5 mg/kg AIIB2 followed by irradiation. IR was administered on day 18.

The radiated cohorts received either a total of 2 GY radiation (200 rad), or a total of 8 Gy. After 4 weeks, animals were sacrificed. Tumor volumes measured at various times are shown in FIG. 7. Tumors were measured and volume estimated by multiplying width×length×depth, measured bi-weekly.

Consistent with the results previously demonstrated, the anti-integrin antibody was shown to have a significant effect on tumor size when used in conjunction with IR therapy. At both 2 Gy and 8 Gy doses, the antibody produced significant reduction in tumor size (i.e. growth) over the use of IR alone, shown as 2 Gy (■) and 8 Gy (▲) in FIG. 7. (The results of IR alone are also shown in FIG. 8). The 8 Gy dose showed the most reduction in tumor size over the control.

Example 7

FIG. 9

In Vivo Treatment of Tumors with Anti-Integrin Antibody After IR

Figure 9:
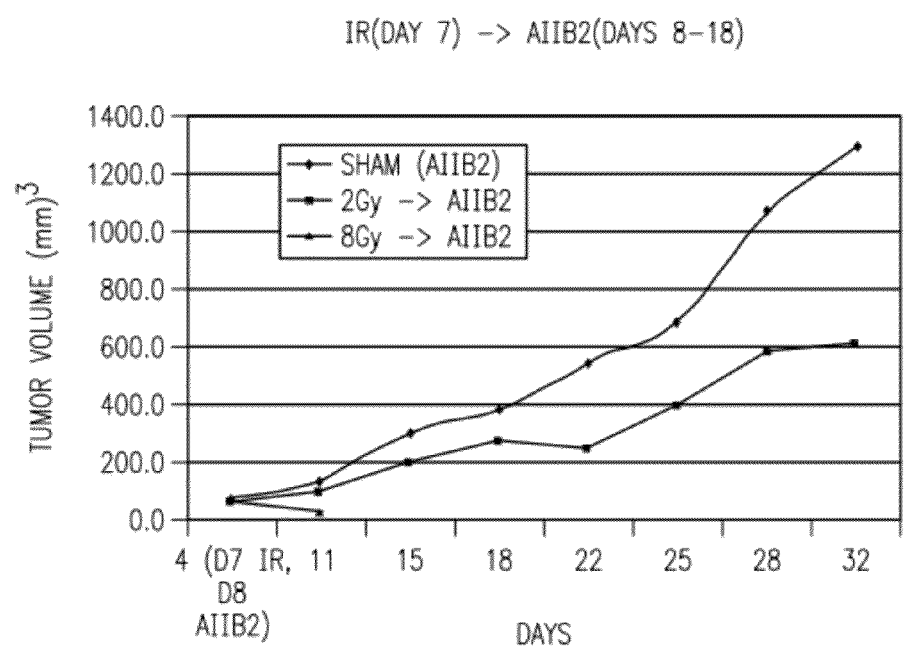
FIG. 9 is a graph showing tumor volume in mice with implanted tumors in which different doses of IR are followed by treatment with an AIIB2 anti-integrin composition.

Results from experiments conducted with mice receiving anti-integrin antibody after different doses of IR are shown in FIG. 9.

Adult female nu −/− mice were implanted with $2 \times 10^7$ MCF-7M1 cells either subcutaneously or into the mammary fat pad on Day 0. Three groups of mice were evaluated: those receiving AIIB2+sham irradiation (i.e. going through the radiation protocol with no radiation); AIIB2 preceded by 2 Gy radiation; and AIIB2 preceded by 8 Gy radiation. The radiated cohorts received either a total of 2 GY radiation (200 rad), or a total of 8 Gy in a single dose on Day 7. Then, on day 8 they received intraperitoneal injections (i.p.) of 5 mg/kg AIIB2.

After 4 weeks, animals were sacrificed. Results expressed as tumor volume in FIG. 9. Tumors are measured and volume is estimated by multiplying width×length×depth, measured bi-weekly.

As shown in FIG. 9, the Sham group, receiving no radiation, had the largest tumor volumes. The tumor volumes of animals receiving 2 Gy were less than half those of the sham group. The animals receiving 8 Gy radiation did not survive beyond 7 days.

At the 2 Gy dose, the antibody produces significant reduction in tumor size (i.e. growth) over the use of IR alone. The 8 Gy dose showed that the radiation doses should be lowered when administering IR prior to anti-integrin therapy. As discussed below, the IR regimen may be tailored with routine experimentation, and/or within known parameters, consistent with clinical practice.

Example 8

FIG. 10

Figure 10A:
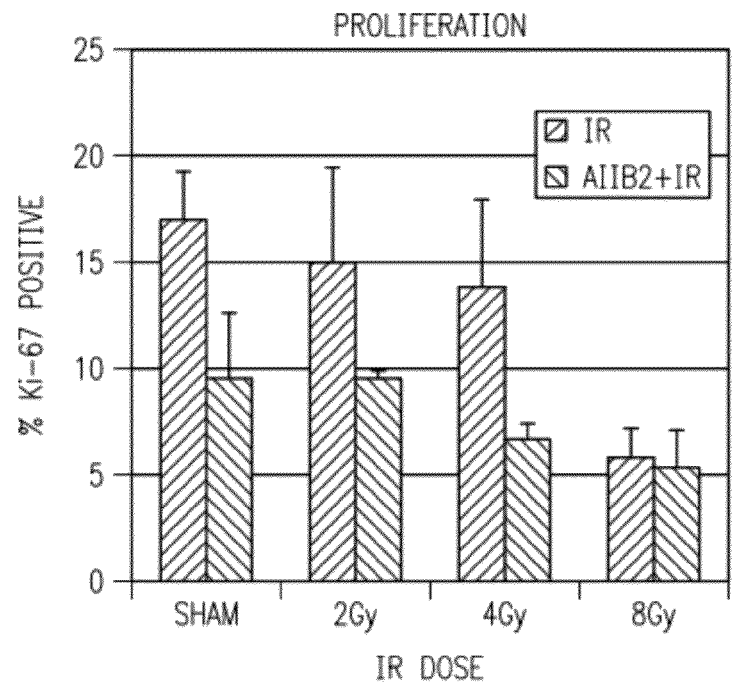
FIG. 10 is a series of bar graphs showing cell proliferation (top panel) and apoptosis (bottom panel) in animals receiving different doses of radiation after anti-integrin composition (AIIIB2) treatment.
Figure 10B:
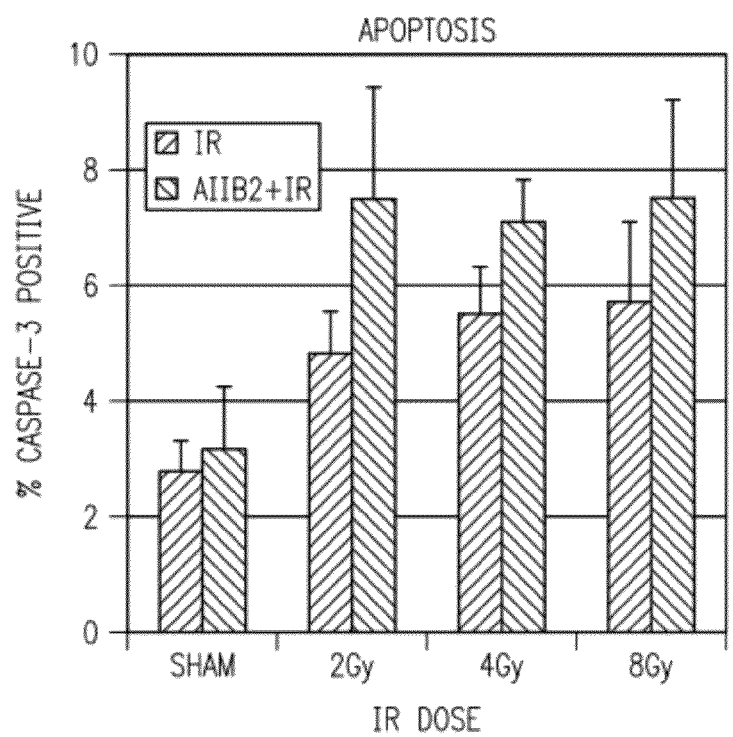

Apoptosis Measurements After In Vivo Treatment of Tumors With Anti-Integrin Antibody and IR FIGS. 10A and 10B show apoptosis data obtained from mice injected with tumor cells. $2 \times 10^6$ T4 cells were injected on Day 0. Beginning on day 4, AIIB2 was administered 5 mg/kg, biweekly. On day 18, either "sham" (radiation protocol, but no radiation), 2 Gy, 4 Gy, or 8 Gy of radiation was administered. On Day 28, the tumors and serum were analyzed ex vivo.

The percentage Ki-67 positive is shown in FIG. 10A. The Ki-67 antibody was first developed by Gerdes and coworkers, who demonstrated the antigen to be present in G1, S, G2 and M phases of continuously cycling cells but absent in G0 cells. Since then, its utility as a proliferative marker has been generally accepted.

The results of FIG. 10A show a significant decrease in proliferation when tumors are treated with anti-integrin antibody and radiation. In this case, a dose of 4 Gy showed the most benefit, in the sense that the AIIB2+IR showed markedly less proliferation than the IR alone. Thus, the administration of anti-integrin antibody in conjunction with IR showed significant reduction in the numbers of dividing cells, even at low IR doses.

FIG. 10B shows the degree of apoptosis in cells receiving either IR alone or IR and antibody, as measured by percent caspase-3 positive cells.

The caspase-3 assay is a measure of apotosis. Execution of apoptosis depends on proper functioning of effector caspases, in particular caspase 3, which is activated on the induction of apoptosis through either the stress-induced pathway or the death receptor-mediated pathway. Thus, high levels of caspase 3 activation should reflect proper functioning of one or both identified apoptosis pathways. As shown in FIG. 10B, more apoptosis was seen in cells from animals that received antibody plus IR for all doses studied. The most significant effect in this experiment was seen at 2 Gy, wherein the cells receiving AIIB2 plus IR exhibited nearly 50% greater apoptosis than the group receiving IR alone (left bars).

Summary

Thus, in carrying out the present method in the context of modifying the cellular response of a carcinoma in a human patient, one would first obtain sufficient amounts of an anti-integrin antibody appropriate for human use. While the presently available mouse or rat antibodies may be appropriate for human use, more likely one would obtain a humanized or fully human antibody shown to inhibit β1 integrin signaling according to the methods discussed above. This monoclonal antibody would be administered at a dosage level of 1-6 µg/kg, as determined by routine experimentation (see below) to provide any measurable effect on tumor cell growth/apoptosis (TUNEL, Annexin V or Ki-67 assays). Beginning, e.g. two days after antibody administration, a standard course of IR therapy is administered to the patient, and tumor cell regression is monitored with MRI or mammogram studies, as is known in clinical practice. The present anti-β1 integrin compositions may be formulated according to known pharmaceutical principles. It may be provided as an oral formulation or an intravenous solution or administered locally via injection or catheterization. It may be a sterile, clear, colorless liquid of pH 7.0 to 7.4, which may contain a small amount of easily visible, white, amorphous, drug particulates. A single-use, 50-mL vial may contain 100 mg of anti-integrin antibody at a concentration of 2 mg/mL and be formulated in a preservative-free solution containing 8.4 mg/mL sodium chloride, 0.88 mg/mL sodium phosphate dibasic heptahydrate, 0.42 mg/mL sodium phosphate monobasic monohydrate, and Water for Injection, USP.

Dosages are determined thorough routine experimentation, depending on the potency of the antibody used. They may be below 1 mg, but typically may be expected to range between 20 and 800 $mg/m^2$ calculated body surface. For example, a 400 $mg/m^2$ initial dosage might be followed by 250 $mg/m^2$ weekly doses. Radiation may be administered prior to or after each dose. The IR regimen may be extended up to once daily, five days per week, for five to seven weeks, as is current clinical practice. The IR dosage may be increased by an order of magnitude or more (e.g. 25 Gy) to approximate dosages given to breast cancer patients. A typical IR dose in a breast cancer patient may be between 180-250 cGy per day.

While the preferred embodiment of the present invention involves the treatment of breast cancer, other solid tumors may be amenable to the present materials and combination therapy as well, as discussed above. β1 integrin inhibition using a monoclonal antibody against β1 integrin results in increased apoptosis and decreased proliferation among malignant cell lines regardless of total β1 integrin expression. 2) The combination of AIIB2 and IR results in enhanced apoptosis, in a radiation dose-dependent manner among malignant cell lines, in both standard 2-D tissue culture plastic, and in a 3-D model. 3) In vivo, AIIB2 resulted in decreased ability for tumors to form, and increased cytotoxic killing in treated versus control tumors. 4) AIIB2 is minimally toxic in vivo. 5) Non-malignant S1, which form acini in 3-D culture resembling normal tissue-like structures, do not exhibit apoptosis after treatment with AIIB2 alone or in combination with IR.

β1 integrin inhibition using an anti-integrin composition is a promising therapeutic which acts against the phenotype of breast cancer cells and may be used to enhance the tumoricidal effect of ionizing radiation.

The apoptotic and cytostatic effect of AIIB2 was observed regardless of the level of β1 integrin expression in several breast cancer cell lines. In vivo, the same results may reasonably be expected.

It is possible that different dose of AIIB2, and sequencing with IR may have different effects. Because others [Reference 17] and we [Reference 43] have previously shown that β1 integrin is persistently upregulated after IR, it is conceivable that this upregulation is associated with refractoriness to apoptosis, and that the addition of AIIB2 after IR is more relevant than prior to IR. Both dosing and sequencing of radiation with chemotherapy have been shown to be clinically significant [Reference 44, 45] resulting in different outcomes for subsets of individual patients. Therefore, one may carry out routine experimentation to determine an it is important to understand the optimal combination of biologic treatments and IR.

If a more pronounced effect is observed with the sequence IR followed by AIIB2, further experiments can be designed to determine if a lower dose of IR or AIIB2 could be used to produce similar results. In addition, mechanistic studies will follow whichever sequence appears to be optimal.

This concept can be carried further to investigate the effects of fractionated IR on tumor cell kill.

Fractionated treatment is more relevant to the clinical setting, and optimal fraction size may be an important parameter in maximizing efficacy and minimizing morbidity. This issue is timely as many efforts are now in place to investigate the use of larger fraction sizes and accelerated treatment courses in the clinical setting. To address this, one may employ the 3-D model, as it will provide a more physiologically relevant context to investigate persistent effects of IR over time. 2 Gy, administered daily over 4 days or a total of 8 Gy administered at one time may be used in the combination therapy. AIIB2 may then be added prior to IR (or at the optimal time, determined from above experiments). These experiments will determine if fractionated treatment results in equal tumor cell kill compared to an equivalent total dose, and if the use of AIIB2 in a fractionated setting is more efficacious than given with a single dose.

There are 3 primary areas where inhibition of β1 integrin signaling and ionizing radiation may be acting synergistically to enhance apoptosis:

a) Cell cycle distribution: Cells in G2/M or late G1 have been shown to be more susceptible to IR-induced apoptosis compared to quiescent or growth arrested cells. β1 integrin inhibition may alter cell cycle distribution to favor radiation-induced apoptosis. For these studies, the combination of AIIB2 and IR resulted in enhanced dose-dependent apoptosis with parallel results observed in standard tissue culture and in 3-D.

b) β1 integrin inhibition may be down modulating the AKT pathway, enhancing cellular susceptibility to apoptosis and IR. Some cell lines (tumors) may have other anti-apoptotic signaling pathways that predominate over the AKT mediated pathway. If we observe an association between AKT and IR-induced apoptosis, one may further directly test the role of AKT by transfecting a dominant-negative form of AKT or alternatively, overexpressing AKT to observe its relationship with IR and AIIB2. Other apoptotic pathways have been implicated in radiation-induced cell killing, including BCL2/BAX mediated pathways, NFKB and P53, for example. Each of these has also been implicated in integrin signaling mediated cell death [Reference 12, 49, 50].

c) Specific α and β integrin heterodimers and also specific substrates may influence response to β1 integrin inhibition and radiation. Among the family of integrin receptors, 10α subunits are capable of partnering with β1 integrin, providing a diversity of ligand binding specificity and in particular cases, unique signaling cascades [Reference 51]. In particular α5β1 has been shown to play a role in cell survival and resistance to cytotoxic therapy, including breast cancer specific chemotherapy [Reference 28, 30]. Different treatments may be suggested if there is a predominant form present. In addition, differential effects of specific integrin heterodimers have been shown to have substrate-specific activity. To test this, different substrates such as fibronectin, laminin and collagen I may be used to plate cells and then test the effect of AIIB2 and IR on these substrates. Activity of specific heterodimers can be tested by inhibiting the α integrin subunit. It is possible that multiple integrins are acting cooperatively within the same cell to effect cellular behavior and that inhibiting β1 integrins globally may be more efficacious that inhibiting any specific heterodimer.

Compositions

Another aspect of the present invention is the use of monoclonal antibodies to both disrupt β1 integrin signaling in the target epithelial (e.g. breast) cell and at the same time deliver ionizing radiation to cells for the purpose of killing cancer cells. Other carcinomas involving epithelial cells that express Preparation of antibodies that contain therapeutic radionucleotides is described in U.S. Pat. No. 6,667,024. That patent describes a therapeutic method used in cancer treatment that involves directing antibodies carrying a therapeutic agent or cytotoxic compound to the diseased tissues. When localized at the disease site, the antibody delivers the therapeutic agent or cytotoxic compound to the cancerous cells. One approach to this methodology involves delivering radioisotopes to the diseased cells. This approach has proven useful in diagnosis where a radioisotope with particular imaging properties is delivered to the targeted diseased tissue. This patent is hereby incorporated by reference for purpose of describing the preparation of a radioimmunotherapeutic antibody reactive with β1 integrin. Also incorporated by reference for purpose of describing the preparation of a radioimmunotherapeutic antibody against β-1 integrin is U.S. Pat. No. 5,246,691, Radioimmunotherapy Using Alpha-particle Emission." Although monoclonal antibodies to β-1 integrin have been prepared previously, novel antibodies which inhibit β-1 integrin are also contemplated by the present invention. As stated above, the term antibody includes human antibodies, humanized mouse or rat antibodies, Fv and FAb fragments. The above cited UK 9707252, now GB patent 2 188 638, described the preparation of chimeric antibodies in which the CDR's have been replaced with those of a different species. According to this method, a rat monoclonal antibody, such as AIIB2 may be used to supply CDR's to a human monoclonal antibody. A mouse is immunized with a β-1 integrin antigen and the splenocytes are fused with a known myeloma partner. The resulting hybridomas are characterized for β-1 integrin inhibition by reacting candidate antibodies with β-1 integrin bearing cells and measuring results of downstream signaling. Integrins have been shown to associate with MAP kinase and receptor tyrosine kinases (RTKs), including c-Met, EGFR and ErbB2, and to cooperate with ligand-induced signaling (see Christofori, "Changing neighbours, changing behaviour: cell adhesion molecule-mediated signalling during tumour progression," EMBO J. 2003 May; 22(10): 2318-2323. Thus measurement of the effects of antibody binding on these downstream signals provides a convenient way to screen for antibodies which have an antagonistic (not an agonistic) effect on β1 integrin signaling.

A suitable antigen may be prepared from a protein or protein fragment encoding human β1 integrin. Gene sequences for such proteins are available at the following GenBank Accession Numbers:

NM_133376, Homo sapiens integrin, beta 1 (fibronectin receptor, beta polypeptide, antigen CD29 includes MDF2, MSK12) (ITGB1), transcript variant 1E, mRNA;

NM_033669 Homo sapiens integrin, beta 1 (fibronectin receptor, beta polypeptide, antigen CD29 includes MDF2, MSK12) (ITGB1), transcript variant 1C-2, mRNA;

NM_033668 Homo sapiens integrin, beta 1 (fibronectin receptor, beta polypeptide, antigen CD29 includes MDF2, MSK12) (ITGB1), transcript variant 1D, mRNA;

NM_033667 Homo sapiens integrin, beta 1 (fibronectin receptor, beta polypeptide, antigen CD29 includes MDF2, MSK12) (ITGB1), transcript variant 1C-1, mRNA;

NM_033666 Homo sapiens integrin, beta 1 (fibronectin receptor, beta polypeptide, antigen CD29 includes MDF2, MSK12) (ITGB1), transcript variant 1B, mRNA; and NM_002211 Homo sapiens integrin, beta 1 (fibronectin receptor, beta polypeptide, antigen CD29 includes MDF2, MSK12) (ITGB1), transcript variant 1A, mRNA.

Protein or proteins fragments expressed from these constructs may be purified and conjugated to adjuvants for improved immunogenicity when immunizing animals against β1 integrin. The different isoforms differ mostly in their cytoplasmic domains and tissue distribution, so that an antibody against the extracellular domain of one isoform would be expected to be active against all isoforms. An area of particular interest for antigen preparation is a conserved region near the N-terminus of the beta subunit, which appears to be of particular importance in ligand binding. See Tuckwell D S, Humphries M J, "A structure prediction for the ligand-binding region of the integrin beta subunit: evidence for the presence of a von Willebrand factor A domain," FEBS Lett. 1997 Jan. 6; 400(3):297-303.

Apart from the above-described antibodies, peptides may be constructed which inhibit β1 integrin function.

For example, it is known that peptides which integrate an Arg-Gly-Asp sequence have potential activity in the inhibition of ligand binding by integrin receptors. An a3b1 integrin-binding peptide from the N-terminal domain of TSP1 (Thrombospondin-1) also modulates endothelial cell proliferation and is a potent inhibitor of endothelial wound repair in vitro. See, Chandrasekaran et al., "Cell Contact-dependent Activation of a3b1 Integrin Modulates Endothelial Cell Responses to Thrombospondin-1, Molecular Biology of the Cell Vol. 11, 2885-2900, September 2000.

Another inhibitory peptide is in development by Attenuon, LLC, San Diego, Calif. and is described in Rabbani, S. A., Khalili, P. and Mazar, A. P. (2003) "A non-RGD based integrin binding peptide (ATN-161) that targets activated alpha-5 beta-1 and alpha-v beta-3 blocks the development of osteolytic skeletal metastases in a xenograft model of breast cancer." Clin Cancer Res 9 (suppl.): 6181S Other candidate peptides are suggested by the disintegrins. Disintegrins represent a group of cysteine-rich peptides occurring in Crotalidae and Viperidae snake venoms, and are potent antagonists of several integrin receptors. A novel disintegrin, obtustatin, was isolated from the venom of the *Vipera lebetina obtusa* viper, and represents the first potent and selective inhibitor of the binding of integrin alpha(1)beta (1) to collagen IV. The primary structure of obtustatin contains 41 amino acids and is the shortest disintegrin described to date. Obtustatin shares the pattern of cysteines of other short disintegrins. However, in contrast to known short disintegrins, the integrin-binding loop of obtustatin is two residues shorter and does not express the classical RGD sequence. Using synthetic peptides, a KTS motif was identified as the integrin-binding sequence. Although Obtustatin is a potent and selective inhibitor of alpha1beta1 integrin, it does not inhibit the closely related integrin alpha2beta1, or a panel of other integrins tested. Importantly, it has recently been reported that obtustatin potently inhibited angiogenesis in vivo in the chicken chorioallantoic membrane assay and in the Lewis lung syngeneic mouse model. Furthermore, Obtustatin also reduced tumor development by 50%, confirming and extending previous results on the relevance of alpha1beta1 integrin to angiogenesis and suggesting that this molecule may serve as a lead for the development of small molecule angiogenesis inhibitors.

Thus there has been described a specific protocol for co-administration of an anti-β1 antibody with ionizing radiation that causes increased apoptosis in tumor cells. Various alternatives to the specifically described embodiments can be achieved using the teachings set forth herein. Accordingly, the present invention should not be construed as limited to the specific embodiments and experiments described, but by the properly interpreted scope of the appended claims.

REFERENCES

1. *Favourable and unfavourable effects on long-term survival of radiotherapy for early breast cancer: an overview of the randomised trials. Early Breast Cancer Trialists' Collaborative Group*. Lancet, 2000. 355(9217): p. 1757-70.
2. Fisher, B., et al., *Twenty-year follow-up of a randomized trial comparing total mastectomy, lumpectomy, and lumpectomy plus irradiation for the treatment of invasive breast cancer*. N Engl J Med, 2002. 347(16): p. 1233-41.
3. Recht, A., et al., *Regional nodal failure after conservative surgery and radiotherapy for early-stage breast carcinoma*. J Clin Oncol, 1991. 9(6): p. 988-96.
4. Morrow, M., et al., *Factors predicting the use of breast-conserving therapy in stage I and II breast carcinoma*. J Clin Oncol, 2001. 19(8): p. 2254-62.
5. Athas, W. F., et al., *Travel distance to radiation therapy and receipt of radiotherapy following breast-conserving surgery*. J Natl Cancer Inst, 2000. 92(3): p. 269-71.
6. Baglan, K. L., et al., *Accelerated partial breast irradiation using 3D conformal radiation therapy (3D-CRT)*. Int J Radiat Oncol Biol Phys, 2003. 55(2): p. 302-11.
7. Baglan, K. L., et al., *The use of high-dose-rate brachytherapy alone after lumpectomy in patients with early-stage breast cancer treated with breast-conserving therapy*. Int J Radiat Oncol Biol Phys, 2001. 50(4): p. 1003-11.
8. Vicini, F., et al., *The emerging role of brachytherapy in the management of patients with breast cancer*. Semin Radiat Oncol, 2002. 12(1): p. 31-9.
9. Whelan, T., et al., *Randomized trial of breast irradiation schedules after lumpectomy for women with lymph node-negative breast cancer*. J Natl Cancer Inst, 2002. 94(15): p. 1143-50.
10. Powell, S., J. Cooke, and C. Parsons, *Radiation-induced brachialplexus injury: follow-up of two different fractionation schedules*. Radiother Oncol, 1990. 18(3): p. 213-20.
11. Paszat, L. F., et al., *Mortality from myocardial infarction following postlumpectomy radiotherapy for breast cancer: a population-based study in Ontario, Canada*. Int J Radiat Oncol Biol Phys, 1999. 43(4): p. 755-62.
12. Lewis, J. M., T. N. Truong, and M. A. Schwartz, *Integrins regulate the apoptotic response to DNA damage through modulation of p53*. Proc Natl Acad Sci USA, 2002. 99(6): p. 3627-32.
13. Fuks, Z., et al., *Effects of extracellular matrix on the response of endothelial cells to radiation in vitro*. Eur J Cancer, 1992. 28A(4-5): p. 725-31.
14. Stevenson, A. F. and C. S. Lange, *Extracellular matrix (ECM) and cytoskeletal modulation of cellular radiosensitivity*. Acta Oncol, 1997. 36(6): p. 599-606.
15. Park, C. C., et al., *Ionizing radiation induces heritable disruption of epithelial cell interactions*. Proc Natl Acad Sci USA, 2003. 100(19): p. 10728-33.
16. Meineke, V., et al., *Ionizing Radiation Modulates Cell Surface Integrin Expression and Adhesion of COLO-320 Cells to Collagen and Fibronectin in Vitro*. Strahlenther Onkol, 2002. 178(12): p. 709-14.
17. Cordes, N., et al., *Ionizing radiation induces up-regulation of functional beta1-integrin in human lung tumour cell lines in vitro*. Int J Radiat Biol, 2002. 78(5): p. 347-57.
18. Hynes, R. O., *Integrins: a family of cell surface receptors*. Cell, 1987. 48(4): p. 549-54.
19. Giancotti, F. G. and G. Tarone, *Positional control of cell fate through joint integrin/receptor protein kinase signaling*. Annu Rev Cell Dev Biol, 2003. 19: p. 173-206.
20. Shaw, L. M., *Integrin function in breast carcinoma progression*. J Mammary Gland Biol Neoplasia, 1999. 4(4): p. 367-76.
21. Zutter, M. M., et al., *Re-expression of the alpha 2 beta 1 integrin abrogates the malignant phenotype of breast carcinoma cells*. Proc Natl Acad Sci USA, 1995. 92(16): p. 7411-5.
22. Weaver, V. M., et al., *Reversion of the malignant phenotype of human breast cells in three dimensional culture and in vivo by integrin blocking antibodies*. J Cell Biol, 1997. 137(1): p. 231-45.11
23. Elliott, B. E., et al., *Anti-beta 1 integrin IgG inhibits pulmonary macrometastasis and the size of micrometastases from a murine mammary carcinoma*. Cell Adhes Commun, 1994. 1(4): p. 319-32.
24. Morini, M., et al., *The alpha 3 beta 1 integrin is associated with mammary carcinoma cell metastasis, invasion, and gelatinase B (MMP-9) activity*. Int J Cancer, 2000. 87(3): p. 336-42.
25. Weaver, V. M., et al., *Reversion of the malignant phenotype of human breast cells in three dimensional culture and in vivo by integrin blocking antibodies*. J Cell Biol, 1997. 137(1): p. 231-45.
26. Sethi, T., et al., *Extracellular matrix proteins protect small cell lung cancer cells against apoptosis: a mechanism for small cell lung cancer growth and drug resistance in vivo*. Nat Med, 1999. 5(6): p. 662-8.

27. Stoeltzing, O., et al., *Inhibition of integrin alpha5beta1 function with a small peptide (ATN-161) plus continuous 5-FU infusion reduces colorectal liver metastases and improves survival in mice.* Int J Cancer, 2003. 104(4): p. 496-503.
28. Aoudjit, F. and K. Vuori, *Integrin signaling inhibits paclitaxel-induced apoptosis in breast cancer cells.* Oncogene, 2001. 20(36): p. 4995-5004.
29. van der Kuip, H., et al., *Adhesion to fibronectin selectively protects Bcr-Abl+ cells from DNA damage-induced apoptosis.* Blood, 2001. 98(5): p. 1532-41.
30. Bhatia, R. and C. M. Verfaillie, *The effect of interferon-alpha on beta-1 integrin mediated adhesion and growth regulation in chronic myelogenous leukemia.* Leuk Lymphoma, 1998. 28(3-4): p. 241-54.
31. Damiano, J. S. and W. S. Dalton, *Integrin-mediated drug resistance in multiple myeloma.* Leuk Lymphoma, 2000. 38(1-2): p. 71-81.
32. Damiano, J. S., et al., *Cell adhesion mediated drug resistance (CAM-DR): role of integrins and resistance to apoptosis in human myeloma cell lines.* Blood, 1999. 93(5): p. 1658-67.
33. Briand, P., et al., *Trisomy 7p and malignant transformation of human breast epithelial cells following epidermal growth factor withdrawal* Cancer Res, 1996. 56(9): p. 2039-44.
34. Zhao, Y. L., C. Q. Piao, and T. K. Hei, *Overexpression of Betaig-h3 gene downregulates integrin alpha5beta1 and suppresses tumorigenicity in radiation-induced tumorigenic human bronchial epithelial cells.* Br J Cancer, 2002. 86(12): p. 1923-8.
35. Onoda, J. M., M. P. Piechocki, and K. V. Honn, *Radiation-induced increase in expression of the alpha IIb beta 3 integrin in melanoma cells: effects on metastatic potential.* Radiat Res, 1992. 130(3): p. 281-8.
36. Hall, D. E., et al., *The alpha 1/beta 1 and alpha 6/beta 1 integrin heterodimers mediate cell attachment to distinct sites on laminin.* J Cell Biol, 1990. 110(6): p. 2175-84.
37. Tomaselli, K. J., C. H. Damsky, and L. F. Reichardt, *Purification and characterization of mammalian integrins expressed by a rat neuronal cell line (PC12): evidence that they function as alpha/beta heterodimeric receptors for laminin and type IV collagen.* J Cell Biol, 1988. 107(3): p. 1241-52.
38. Werb, Z., et al., *Signal transduction through the fibronectin receptor induces collagenase and stromelysin gene expression.* J Cell Biol, 1989. 109(2): p. 877-89.
39. Wang, F., et al., *Reciprocal interactions between beta1-integrin and epidermal growth factor receptor in three-dimensional basement membrane breast cultures: a different perspective in epithelial biology.* Proc Natl Acad Sci USA, 1998. 95(25): p. 14821-6.
40. Armulik, A., *Splice variants of human beta 1 integrins: origin, biosynthesis and functions.* Front Biosci, 2002. 7: p. d219-27.
41. Tagliabue, E., et al., *Prognostic value of alpha 6 beta 4 integrin expression in breast carcinomas is affected by laminin production from tumor cells.* Clin Cancer Res, 1998. 4(2): p. 407-10.
42. Seo, D. W., et al., *TIMP-2 mediated inhibition of angiogenesis: an MMP-independent mechanism.* Cell, 2003. 114(2): p. 171-80.
43. Park, C., et al., *Cell-ECM mediated radiation response in breast cancer: beta1 integrin as a potential molecular target.* Int J Radiat Oncol Biol Phys, 2003. 57(2 Suppl): p. S161. 12
44. Dubey, A., et al., *Concurrent CMF and radiation therapy for early stage breast cancer: results of a pilot study.* Int J Radiat Oncol Biol Phys, 1999. 45(4): p. 877-84.
45. Recht, A., et al., *The sequencing of chemotherapy and radiation therapy after conservative surgery for early-stage breast cancer.* N Engl J Med, 1996. 334(21): p. 1356-61.
46. Wang, X. Q., P. Sun, and A. S. Paller, *Inhibition of integrin-linked kinase/protein kinase B/Akt signaling: mechanism for ganglioside-induced apoptosis.* J Biol Chem, 2001. 276(48): p. 44504-11.
47. Pankov, R., et al., *Specific beta1 integrin site selectively regulates Akt/protein kinase B signaling via local activation of protein phosphatase 2A.* J Biol Chem, 2003. 278 (20): p. 18671-81.
48. Damiano, J. S., *Integrins as novel drug targets for overcoming innate drug resistance.* Curr Cancer Drug Targets, 2002. 2(1): p. 37-43.
49. Weaver, V. M., et al., *beta4 integrin-dependent formation of polarized three-dimensional architecture confers resistance to apoptosis in normal and malignant mammary epithelium.* Cancer Cell, 2002. 2(3): p. 205-16.
50. Truong, T., et al., *Modulation of DNA damage-induced apoptosis by cell adhesion is independently mediated by p53 and c-Abl.* Proc Natl Acad Sci USA, 2003. 100(18): p. 10281-6.

What is claimed is:

1. A method for reducing proliferation of tumor cells, wherein said cells express β1 integrin, comprising the steps of:
   (a) delivering to said tumor cells an inhibitory anti-β1 integrin composition comprising an inhibitory agent that binds to all heterodimers of β1 integrin, said agent being an antibody selected from the group consisting of a human monoclonal antibody, an antibody fragment having a human Fv portion, and a single chain recombinant antibody having Fv portion, wherein said Fv portions antagonize a human β1 integrin, and
   (b) delivering to said tumor cells ionizing radiation in a dose effective to reduce cellular proliferation, whereby said reducing proliferation is greater than a reduction caused by either the anti-β1 integrin composition alone or the radiation alone.

2. The method of claim 1 wherein said anti-β1 integrin antibody is a human monoclonal antibody.

3. The method of claim 1 wherein said anti-β1 integrin antibody is an antibody fragment.

4. The method of claim 1 wherein said delivering radiation of step (b) is carried out after delivering said anti-β1 integrin antibody of step (a).

5. The method of claim 4 wherein said ionizing radiation is in a dose of 2-6 Gy.

6. The method of claim 4 wherein said radiation is delivered at a rate of 0.25 to 6 Gy per minute.

7. The method of claim 6 wherein said radiation is delivered at a rate of less than 2 Gy per minute.

8. The method of claim 1 wherein said tumor cells are epithelial cells.

9. The method of claim 2 wherein said antibody has attached thereto a radioisotope for delivering ionizing radiation.

10. A method of modulating cellular apoptosis comprising the steps of:
   (a) providing a cell that is adherent to an extracellular matrix having components binding to cellular β1 integrin, (b) delivering to said cell an inhibitory anti-β1 integrin composition comprising an inhibitory agent that binds to all heterodimers of β1 integrin, said agent being an antibody, wherein said anti-β1 integrin antibody is a human, mouse or rat monoclonal antibody, and (c) delivering to said cell ionizing radiation whereby increased apoptosis is greater than an increase caused by the composition alone or the radiation alone.

11. A method of reducing epithelial cell tumor growth in a mammalian subject, comprising the steps of:

(a) administering to the subject at least 2 Gy of ionizing radiation directed to the epithelial cell tumor; and (b) administering to the subject an anti-β1 integrin composition comprising an inhibitory agent that binds to all heterodimers of β1 integrin, said agent being an, whereby growth of the epithelial cell tumor is reduced, wherein said anti-β1 integrin antibody is a human monoclonal antibody or an Fv antibody fragment.

12. The method of claim 11 wherein said delivering radiation of step (b) is carried out after delivering said anti-β1 integrin composition.

13. The method of claim 12 wherein said ionizing radiation is in a total dose of 2-20 Gy.

* * * * *

UNITED STATES PATENT AND TRADEMARK OFFICE
CERTIFICATE OF CORRECTION

| | | |
|---|---|---|
| PATENT NO. | : 8,246,952 B2 | Page 1 of 1 |
| APPLICATION NO. | : 12/575411 | |
| DATED | : August 21, 2012 | |
| INVENTOR(S) | : Catherine Park and Mina J. Bissell | |

It is certified that error appears in the above-identified patent and that said Letters Patent is hereby corrected as shown below:

Claim 11, column 24, line 3, after "an" insert --antibody--.

Signed and Sealed this
Thirteenth Day of November, 2012

David J. Kappos
*Director of the United States Patent and Trademark Office*